June 20, 1933. F. H. HOWARD Plant Pat. 67
HYBRID TEA ROSE
Filed Sept. 22, 1932
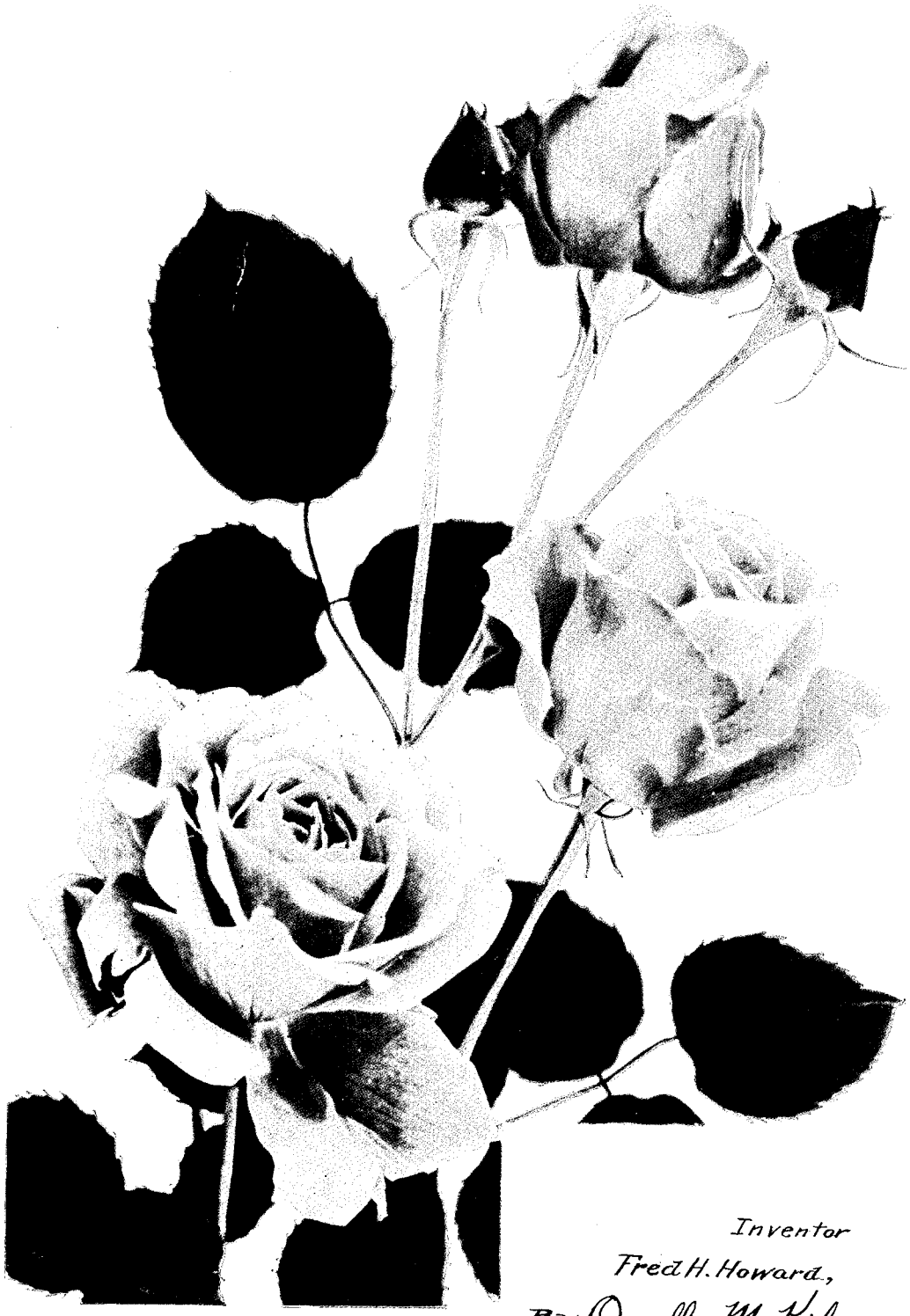
Inventor
Fred H. Howard,
By Orville M. Kile
Plant Patent Agent Patented June 20, 1933 Plant Pat. 67

UNITED STATES PATENT OFFICE

FRED H. HOWARD, OF MONTEBELLO, CALIFORNIA, ASSIGNOR TO MINNIE JONES HOWARD, OF MONTEBELLO, CALIFORNIA

HYBRID TEA ROSE

Application filed September 22, 1932. Serial No. 634,428.

My present invention relates to improvements in fragrant red hybrid tea roses. The objects of my improvements are, briefly stated, to provide a rose of the type mentioned having flowers of a new and distinctive shade of color, large, faultless and camellia-like form, having superior producing and keeping qualities and other desirable characters.

This new rose is the result of definite breeding efforts carried on by myself and my associates at Montebello, California, and originated from a cross between the well-known variety Premier Supreme and the variety known as McGredy's Scarlet, the first named being the seed parent and the second the pollen parent.

The accompanying illustrations show in full color two tight buds and three flowers in various stages of maturity, also stems and foliage, all depicted as nearly as possible in their true forms and colors.

The following is a detailed description of this rose plant and flower:

*The bush or plant.*—Under ordinary good greenhouse conditions grows 4½ to 5 feet high. It is a vigorous grower and is exceedingly productive. Plants grown under greenhouse forcing conditions, benched 15″ by 15″, produce ordinarily 40 to 50 salable flowers each, and often as high as 60 salable flowers are taken from a single plant in a year. This variety produces little blind wood and when pinched off the branch breaks freely, producing two and often three shoots.

*Stems.*—Stoutish, green, beset with small spines for the first 6 to 8 inches below blossom, and below first leaf branch has distinct but not numerous pinkish thorns set perpendicular to the stem.

*Leaf branches.*—On flower-bearing stems 4 to 5 inches long, ordinarily having 5 leaflets except on first branch below the blossom which has 3 leaflets. There is generally a rudimentary leaf from ¼ to 1¼ inches long above the first leaf branch. The leaflets are of approximately "forest green" color (Plate XVII Ridgeway's Color Standard and Nomenclature), only slightly glabrous, ovate, and the edges are cut by sharp-pointed, deep but rather small notches or serrations. The central stem or petiole from which the leaflets spring bears one to four spines or small thorns pointing downward.

*Stipules.*—Quite small and narrow, with slender pointed but non-curled tips.

*Hips.*—½ inch long, wide and tapering.

*Buds.*—Relatively short for their width, those measuring 1 inch long having a width at the base of about ¾ inch. Buds are ordinarily 1¼ inches long and about ⅞ inch wide. Despite their basal width, the buds form a sharp point at the top. The tight rolled buds generally show decided green areas at the bases of the outer petals and in streaks up the central portions of one or two of the outer exposed petals.

*Sepals.*—Normally 5 in number, relatively short in proportion to the large size of the blossom. The usual length of sepals is 1½ inches but an occasional sepal will become slightly branched and foliaceous and reach a length of 1½ inches. In the main, however, the sepals are rather narrow and either smooth and regular along their edges or with but a single pair of small offshooting points.

*Blossoms.*—Are very large, ordinarily being 3½ to 4 inches across the top when grown in greenhouses in the vicinity of Philadelphia in the month of March, as shown in the accompanying illustrations. Under some conditions, however, the blossoms attain a diameter of 5½ to 6 inches. The form may be described as "perfect" in that the petal arrangement of a normal blossom is very regular and gives an effect referred to as "camellia-like."

The flower is decidedly double, having in the month of March in the latitude of Philadelphia, in a typical specimen, 50 large petals, 30 medium sized petals, 25 small petals and a dozen or more rudimentary petals. The flower also contains a large number of yellow anthers mounted on white stamens, and a large number of white or pinkish pistils.

The color of this rose varies somewhat as between specimens and with the degree of maturity. It is a color not found in any other variety of rose known to the originator. The color shade of the opening bud is darker than that of the more mature flower, and there is no color shade in Ridgeway's Color Standard and Nomenclature that properly indicates this shade. The nearest approach is "Tyrian rose" shown on Plate XII. But the newly opening bud is darker than Tyrian rose and, moreover, has a velvety surface that reflects the light in a variety of shades when viewed from different angles. As the flower matures and opens the predominating color shade becomes lighter. This shade is approximately "rose color" (Plate XII, of Ridgeway's Color Standard and Nomenclature). However the outer two or three rows of petals retain their darker shade. In practically all cases the inside surface of the petals is darker than the outside. The central petals all have a fine edging of lighter shade. The veining is scarcely visible.

A distinctive character is found in the fact that each petal in the outer row of 5 or 6 petals has a white streak down its center visible on the inside only. The other petals do not have this streak effect until the center of the flower is approached, where a dozen or more of the medium-sized petals may have this same effect.

The flower is intensely fragrant and has extraordinary keeping qualities. When cut as an opening bud and kept in water, the flower will last fully ten days.

What I claim as new is:

The variety of hybrid tea rose herein shown and described, characterized particularly by its vigorous growth and exceptional producing powers, and its fragrant blossoms of large size, camellia-like form, and distinctive shades of intense red color.

In testimony whereof I affix my signature.

FRED H. HOWARD.